United States Patent [19]

Shulman

[11] Patent Number: 5,206,267
[45] Date of Patent: Apr. 27, 1993

[54] PAIN CONTROLLING COMPOSITION AND METHOD OF PREPARATION

[76] Inventor: Morton Shulman, 1115 Thorntree La., Highland Park, Ill. 60035

[21] Appl. No.: 870,767

[22] Filed: Apr. 20, 1992

Related U.S. Application Data

[63] Continuation-in-part of Ser. No. 697,618, May 9, 1991, abandoned.

[51] Int. Cl.$^5$ ............................................. A61M 31/24
[52] U.S. Cl. .................................... 514/536; 514/535
[58] Field of Search ................................ 514/535, 536

[56] References Cited

U.S. PATENT DOCUMENTS 3,337,400  8/1967  Smith ................................ 514/171
4,599,354  7/1986  Shulman ............................ 514/530

FOREIGN PATENT DOCUMENTS 0336901   3/1989   European Pat. Off.
53-121920 3/1978   Japan.
1-143829  6/1989   Japan.
WO9114455 10/1991  PCT Int'l Appl.
784659    10/1957  United Kingdom.

OTHER PUBLICATIONS

Chem. Abst. 112-42616s (1990).
Chem. Abst. 113-46279c (1990).
Juni, et al, "Drug Release Through A Silicone Capsular Membrane . . . ", Journal of Membrane Science, 1975, vol. 5, p. 295.
Shulman, "Treatment of Cancer Pain . . . ", Regional Anesthesiology, Jan.-Mar., 1987, vol. 12, p. 1.
Shulman, "Epidural Butamben . . . ", Anesthesiology, Sep. 1987, vol. 67, p. A245.
Shulman, "Intercostal Nerve Block . . . ", Anesthesiology, Sep. 1989, vol. 71, p. A737.
Shulman, et al., "Effect of Epidural . . . ", Regional Anesthesiology, May-Jun., 1990, vol. 15, p. 142.
Korsten, et al., "Long-lasting Epidural Sensory Blockade . . . ", Anesthesiology, Sep. 1990, vol. 73, p. 491.
Grouls, et al., "Butyl-p-aminobenzoate . . . ", Pharm. Weekbl., Jan. 1991, vol. 13, pp. 2524-1.
Physicians' Desk Reference, Edward R. Barnhart, Medical Economics Company, Inc., 1989, p. 1106.

*Primary Examiner*—S. J. Friedman
*Attorney, Agent, or Firm*—Marshall, O'Toole, Gerstein, Murray & Bicknell

[57] ABSTRACT

A composition, for producing pain relief in a body region, comprises a sterile, stable suspension of butyl aminobenzoate in a non-toxic, aqueous carrying medium in which the butyl aminobenzoate is substantially insoluble. The aqueous carrying medium consists essentially of water as the major constituent and a suspending agent composed of (a) polyethylene glycol and (b) a wetting agent for the butyl aminobenzoate, with a ratio of (a) to (b) in the range of about 50/1 to 125/1. The butyl aminobenzoate is milled to a particle size in the range of about 5 to 50 microns in the presence of the suspending agent.

26 Claims, No Drawings

PAIN CONTROLLING COMPOSITION AND METHOD OF PREPARATION

This application is a continuation-in-part of application Ser. No. 07/697,618, filed May 9, 1991, now abandoned.

BACKGROUND OF THE INVENTION

The present invention relates generally to pain controlling compositions and more particularly to a pain controlling composition containing butyl aminobenzoate.

Shulman U.S. Pat. No. 4,599,354 discloses a pain controlling composition consisting essentially of a sterile, stable suspension of butyl aminobenzoate in a non-toxic, aqueous carrying medium in which the butyl aminobenzoate is insoluble; and the disclosure thereof is incorporated herein by reference.

The butyl aminobenzoate constitutes about 5-15 wt. % of the composition, and the aqueous carrying medium consists essentially of water as the major constituent and up to about 10 wt. % polyethylene glycol as a suspending agent for the butyl aminobenzoate.

The composition is typically administered by injection to a body region where pain control is desired, and it is important that the butyl aminobenzoate be uniformly distributed, as a physical suspension, throughout the aqueous carrying medium at the time the composition is administered.

Difficulties have been encountered in obtaining the desired physical suspension or, once obtained, in maintaining it. In some instances when polyethylene glycol has been used as the suspending agent, there was floatation by the butyl aminobenzoate. Attempts to employ polysorbate 80, a wetting agent, to suspend the butyl aminobenzoate have resulted in settling by the butyl aminobenzoate.

SUMMARY OF THE INVENTION

The present invention minimizes or eliminates the difficulties in obtaining and/or maintaining the desired physical suspension. In accordance with the present invention, the aqueous carrying medium contains, as a suspending agent for the butyl aminobenzoate, both (a) polyethylene glycol in an amount sufficient to prevent the butyl aminobenzoate from settling and (b) a wetting agent, for the butyl aminobenzoate, in an amount sufficient to prevent the butyl aminobenzoate from floating. A preferred wetting agent for the butyl aminobenzoate is polysorbate 80. Generally, the composition comprises 5-15 wt. % butyl aminobenzoate and 1-10 wt. % polyethylene glycol having a molecular weight in the range 1000-5000. The ratio of polyethylene glycol to wetting agent is generally about 50/1 to 125/1. Preferably, the ratio is in the range of about 75/1 to 100/1, and most preferably in the range 80/1 to 85/1, particularly when the wetting agent is polysorbate 80.

The composition described above is sterilized in a sealed container, and the butyl aminobenzoate is mechanically milled to a desired mean particle size in the range 5 to 50 microns, in the presence of the suspending agent, in the sealed container. Particle size reduction employing a series of freeze/fracture cycles should be avoided.

Other features and advantages are inherent in the composition and method of preparation claimed and disclosed or will become apparent to those skilled in the art from the following detailed description.

DETAILED DESCRIPTION

A composition in accordance with the present invention may be prepared employing 10 wt. % butyl aminobenzoate in an aqueous carrying medium. The aqueous carrying medium consists essentially of water as the major component and a non-toxic suspending agent composed of (a) polyethylene glycol having a molecular weight of preferably about 3350 and (b) polysorbate 80, in ratios of (a) to (b) of 50/1 to 125/1.

Polysorbate 80 is a wetting agent for butyl aminobenzoate. It is a mixture of oleate esters of sorbitol and sorbitol anhydrides, consisting predominantly of the monoester, condensed with approximately 20 moles of ethylene oxide. Polysorbate 80 has an average molecular weight of about 1300.

Other non-toxic wetting agents may be used if they can perform the desired anti-floatation function performed by polysorbate 80. Logical candidates would include other polysorbates relatively similar to polysorbate 80, e.g. polysorbate 81 and polysorbate 85. Other polysorbate candidates would include polysorbate 61 and polysorbate 65, for example.

The aqueous carrying medium typically contains about 0.9 wt. % sodium chloride. The pH of the composition containing the ingredients described above is adjusted to 4, typically by the addition of concentrated hydrochloric acid. Dextran is excluded from the composition.

The composition can be processed by placing the composition in a vial containing a bar magnet. The vial is sealed, and the composition is subjected to a sterilizing operation while still in the vial. During sterilization, the butyl aminobenzoate melts, and upon cooling following sterilization, the butyl aminobenzoate precipitates as particles which must be subjected to a milling operation in order to reduce them to a size, in the range 5-microns, suitable for administering by injection. This can be accomplished by magnetic stirring, a conventional operation which causes the bar magnet in the vial to rotate rapidly within the vial, milling the particles of butyl aminobenzoate as the bar magnet rotates.

More particularly, the vial is fixed in a vertical position with the bar magnet horizontally disposed at the bottom of the vial close to and above a second horizontally disposed bar magnet located outside the vial. The second bar magnet is mounted for rotation at high speeds about a vertical axis, and this induces high speed rotation of the bar magnet within the vial, creating a stirring and milling action within the vial. The magnetic stirring operation is continued for 48-100 hours, for example, (typically 72 hours) until the butyl aminobenzoate particles have been milled to the desired size.

Ball milling is an alternative procedure for reducing the butyl aminobenzoate particles to the desired size. When one employs ball milling, the composition is sterilized in a sealed cylinder containing milling balls. During cooling following sterilization, the cylinder is rotated about its axis, in a horizontal disposition, and rotation is continued until the butyl aminobenzoate particles in the cylinder are ground down to the desired size by the movement the balls undergo as the cylinder is rotated.

The composition was determined to be bactericidal (capable of killing bacteria). Accordingly, the composition may be handled, after the above-described manufacturing operation, under less meticulous precautions than would be required for compositions which are not bactericidal. Even if the present composition were to become contaminated, one need only store the composition for a period of time before use to enable the bactericidal property to take effect; and one need not add to the composition a separate preservative, i.e. an ingredient which is bacteristatic (capable of preventing bacterial growth) or bactericidal.

The upper limit for butyl aminobenzoate, as a percentage of the suspension, should be about 15 wt. %, although 10 wt. % is a more practical upper limit because viscosity increases with increased butyl aminobenzoate content, and above 10 wt. %, the composition can become too viscous. Decreasing the butyl aminobenzoate content decreases the efficacy of the composition, and below 5 wt. % butyl aminobenzoate, the efficacy drops off too much, although a composition containing 2.5 wt. % butamben can be effective with repeated injections.

For a butyl aminobenzoate content in the range of about 5-15 wt. %, there should be a polyethylene glycol content in the range of about 1-10 wt. %, as a percentage of the suspension. Polyethylene glycol prevents the butyl aminobenzoate from settling in the aqueous carrying medium, and the amount of polyethylene glycol which should be employed is that amount which will prevent the particular butyl aminobenzoate content in the composition from settling out. Generally, for the range of butyl aminobenzoate employed in accordance with the present invention (5-15 wt. %) a polyethylene glycol content above 10% is unnecessary and incorporates too much extraneous matter into the composition.

In a suspension containing 5 wt. % butyl aminobenzoate and 10 wt. % polyethylene glycol, the polyethylene glycol is 10.5 wt. % of the aqueous carrying medium; and in a suspension containing 15 wt. % butyl aminobenzoate and 10 wt. % polyethylene glycol, the polyethylene glycol is 11.8 wt. % of the aqueous carrying medium. Both of these percentages (10.5 wt. % and 11.8 wt. %) are substantially consistent with the amount (about 10 wt. %) described in Shulman U.S. Pat. No. 4,599,354 as the upper percentage for the range of polyethylene glycol in the aqueous carrying medium there.

The wetting agent should be present in an amount sufficient to prevent the butyl aminobenzoate from floating. This depends upon both (1) the amount of butyl aminobenzoate in the composition and (2) the amount of polyethylene glycol in the composition. Generally, the ratio of (a) polyethylene glycol to (b) wetting agent should be in the range 50/1 to 125/1. One should avoid employing too much wetting agent because that can cause the butyl aminobenzoate to settle out of the suspension. Preferably, the ratio of (a) to (b) is 75/1 to 100/1, and most preferably about 80/1 to 85/1, particularly when the wetting agent is polysorbate 80.

Polysorbate 80 is preferably added to the composition before the composition is sterilized, but the polysorbate 80 may also be added either after sterilization and before milling or after milling. The last two types of addition require breaking the seal on the vial after sterilization, but breaking the seal is probably harmless because of the apparent bactericidal nature of the composition.

Tests were conducted to determine the effect of various ratios of (a) polyethylene glycol and (b) polysorbate 80 on maintaining the butyl aminobenzoate in physical suspension. The test compositions contained 10 wt.% butyl aminobenzoate and were prepared in accordance with the description set forth above, employing magnetic stirring. The test results are tabulated below.

| Sample No. | (a) Wt. % Polyethylene Glycol | (b) Wt. % Polysorbate 80 | Ratio of (a) to (b) | Results |
|---|---|---|---|---|
| 1 | 2.5 | 0.05 | 50/1 | Thin, non-viscous suspension; marked settling |
| 2 | 2.5 | 0.03 | 83/1 | Thin, non-viscous suspension; minimal settling |
| 3 | 2.5 | 0.025 | 100/1 | Thin, non-viscous suspension; questionably thicker than Sample No. 2; questionable floatation |
| 4 | 2.5 | 0.02 | 125/1 | Semi-thin suspension; some viscosity; definite floatation |
| 5 | 1.0 | 0.01 | 100/1 | Thin suspension; questionable viscosity; no floatation or settling |
| 6 | 1.0 | 0.015 | 67/1 | Similar to Sample No. 5 |
| 7 | 1.5 | 0.015 | 100/1 | Similar to Sample No. 5 |
| 8 | 1.5 | 0.02 | 75/1 | Viscous suspension; floatation |
| 9 | 1.5 | 0.025 | 60/1 | Similar to Sample No. 5 |
| 10 | 2.0 | 0.025 | 80/1 | Some viscosity; stable suspension |

With respect to the ten samples tabulated above, sample numbers 1, 4 and 8 were considered to be marginally acceptable, while all the other samples were considered to be substantially totally acceptable. The best results were obtained with sample number 2 which provided a thin, non-viscous suspension with minimal settling employing 2.5 wt. % polyethylene glycol and 0.03 wt. % polysorbate 80, with a ratio of (a) to (b) of 83/1.

From the foregoing it was concluded that the ratio of (a) polyethylene glycol to (b) polysorbate 80 (i.e. wetting agent) should be within the range 50/1 to 125/1, preferably 75/1 to 100/1, and most preferably 80/1 to 85/1.

As noted above, the results set forth in the tabulation were obtained employing a procedure in which the particles of butyl aminobenzoate were milled to the desired size by magnetic stirring. A freeze/fracture method was also tried as a procedure for reducing the particle size of the butyl aminobenzoate, but the results obtained were unsatisfactory. More particularly, percentages of polyethylene glycol and polysorbate 80, similar to those listed in the tabulation, were employed, and ratios of (a) polyethylene glycol to (b) polysorbate 80 in the range 83/1 to 250/1 were employed. The compositions tested were also otherwise similar to the ten samples tabulated above. Even after seven cycles of freezing and then shaking while defrosting, the particles obtained were not as uniform or as small as those obtained when employing magnetic stirring. All of the resulting compositions settled.

A similar composition but containing 0.025 wt. % polysorbate 80 as the only suspending ingredient was also tried, but it produced a suspension less stable than any of the ten samples tabulated above; the butyl aminobenzoate settled.

Compositions containing 5 wt. % and 2.5 wt. % butamben may be employed, although repeated injections may be required if the initial injection (or injections) do not produce sufficient pain relief. A procedure employing more than one injection is sometimes required with a composition containing 10 wt. % butamben. Examples of compositions containing 2.5 and 5.0 wt. % butamben, prepared in accordance with the present invention, are set forth below, with quantities being listed in wt. %:

| Example | Butamben | Polyethylene Glycol 3350 | Polysorbate 80 |
| --- | --- | --- | --- |
| A | 2.5 | 1.5 | 0.015 |
| B | 5.0 | 1.0 | 0.02 |

The ratios of polyethylene glycol 3350 to polysorbate 80 in Examples A and B are 100/1 and 50/1 respectively.

One may typically employ respective ranges of 0.5 to 3.0 wt. % polyethylene glycol 3350 (PEG 3350) and 0.006–0.025 wt. % polysorbate 80 (PS 80), for example, in compositions containing either 2.5 wt. % or 5.0 wt. % butamben. The foregoing ranges are preferred ranges. Permissible ranges comprise 0.5 to 5.0 wt. % PEG 3350 and 0.005–0.05 wt. % PS 80, for example.

Compositions such as Examples A and B can be made by initially preparing a composition containing 10 wt. % butamben (BAB), in the manner described above, and then diluting the 10 wt. % BAB composition with an aqueous saline solution (0.9 wt % NaCl) until the desired butamben concentration (e.g. 2.5 wt. % or 5.0 wt. %) is obtained. When employing such a procedure, it is desirable to use about 0.03 wt. % polysorbate 80 (PS 80), rather than a smaller amount (such as 0.025 wt. % PS 80 as in a typical example employing 10 wt. % butamben) to prevent the occasional occurrence of floccing.

As an alternative to employing the dilution procedure described in the preceding paragraph, one may combine all the ingredients in the desired proportions initially, and use the magnetic milling and stirring procedure or the ball milling procedure described above. The resulting mixture initially may tend to floc when the butamben content is 2.5 or 5.0 wt. %, forming a loose, feathery suspension; but if allowed to stand for 48 hours, the loose feathery suspension becomes a fine powder which requires merely shaking a few times to provide a good suspension suitable for injection.

As previously noted, the suspending agent contains both polyethylene glycol (PEG) and polysorbate 80 (PS 80). If PS 80 alone were employed as the suspending agent, the butamben (BAB) would settle as a relatively shallow, dense layer on the bottom of the container for the composition. Particles of BAB would be relatively closely packed, and if the container (e.g. a vial) were to be inverted, the layer of BAB would tend to remain at the location where it had previously settled.

The use of PEG in combination with PS 80, in accordance with the present invention, prevents the formation of a shallow, dense layer of BAB on the bottom of the container; instead, the same amount of BAB forms a relatively deep, less dense layer composed of BAB particles which are not closely packed together. When shaken a few times, a good suspension is formed, suitable for injection.

The BAB particles in a suspension containing both PEG and PS 80 will not be inclined to settle out so much when a slow injection procedure is used, and relatively little shaking need be employed to maintain the suspension, compared to the case where no PEG was employed with the PS 80 in the suspending agent. The latter composition (no PEG) requires repeated shaking when used with a slow injection procedure, or else the BAB particles will settle out relatively rapidly.

A composition containing a substantially smaller concentration of BAB than 10 wt. % (e.g. 2.5 wt. % or 5.0 wt. % BAB) is more mobile and has better flow characteristics than 10 wt. % BAB. For example, at 37° C. the more dilute 2.5 wt. % suspension of BAB has a shear resistance of 2.6 centipoise versus a shear resistance of 18.8 centipoise for 10 wt. % BAB. The more concentrated, less mobile suspension (10 wt. % BAB) can produce small aggregates or clumping of BAB particles at or near the injection site, and that is undesirable. In the less concentrated, more mobile suspensions (e.g. 2.5 wt. % BAB), clumping is much less of a problem, and the increased mobility is desirable in that it better enables the suspension, upon injection, to flow to the desired location (e.g. around a given nerve).

Tests were conducted on chronic pain patients, employing Example A described above (2.5 wt. % BAB). Peripheral nerve blocks were administered to sixteen patients with chronic pain syndromes: 14 had chronic benign pain and 2 had pain of metastatic cancer. The patients rated pain relief as good, fair or poor. Successful pain relief was defined as good pain relief that lasted for longer than four weeks. Patients were offered a repeat injection if there was no immediate pain relief. A repeat injection was usually administered at least 24 hours after a previous injection, typically three days or more in the case of out-patients. Five patients received one injection, and two of these patients had successful pain relief. Nine patients received two injections, and seven of these patients had successful pain relief. Three injections and four injections were given to one patient each, and each patient had successful pain relief.

Seven of the sixteen patients treated with 2.5 wt. % BAB had received previous treatment with a 10 wt. % BAB suspension. Five of the seven previously treated patients had experienced good pain relief for more than six months, and they were treated with 2.5 wt. % BAB when the pain eventually returned; two of the previous treatments had been unsuccessful. Of the five who had previously been treated successfully with 10 wt. % BAB, four were subsequently treated successfully with 2.5 wt. % BAB while one such subsequent treatment was unsuccessful. Of the two who had previously been treated unsuccessfully with 10 wt. % BAB, one was subsequently treated successfully with 2.5 wt. % BAB while one other such subsequent treatment was unsuccessful. No complications were observed with the 2.5 wt. % BAB suspension.

The foregoing detailed description has been given for clearness of understanding only, and no unnecessary limitations should be understood therefrom, as modifications will be obvious to those skilled in the art.

I claim:

1. A composition for producing pain relief in a body region by introduction of said composition under the skin, said composition consisting essentially of:

a sterile, stable suspension of butyl aminobenzoate in a non-toxic, carrying medium in which said butyl aminobenzoate is substantially insoluble;

said carrying medium consisting essentially of water as the major constituent and a suspending agent composed of (a) polyethylene glycol having a molecular weight of at least about 1000 and (b) a wetting agent for said butyl aminobenzoate;

said butyl aminobenzoate being present in effective amounts up to about 15 wt. % of said suspension;

said polyethylene glycol being present in an amount sufficient to reduce substantially the tendency of said butyl aminobenzoate to settle in said carrying medium;

said wetting agent being present in an amount sufficient to prevent said butyl aminobenzoate from floating in said carrying medium;

the ratio of (a) said polyethylene glycol to (b) said wetting agent being at least about 50/1.

2. A composition for producing pain relief in a body region by introduction of said composition under the skin, said composition consisting essentially of:

a sterile, stable suspension of butyl aminobenzoate in a non-toxic, carrying medium in which said butyl aminobenzoate is substantially insoluble;

said carrying medium consisting essentially of water as the major constituent and a suspending agent composed of (a) polyethylene glycol and (b) a wetting agent for said butyl aminobenzoate;

said butyl aminobenzoate being present in effective amounts up to about 15 wt. % of said suspension;

said polyethylene glycol being present in an amount, up to about 10 wt. % of said suspension, sufficient to reduce substantially the tendency of said butyl aminobenzoate to settle in said carrying medium;

said wetting agent being present in an amount sufficient to prevent said butyl aminobenzoate from floating in said carrying medium;

the ratio of (a) said polyethylene glycol to (b) said wetting agent being at least about 50/1.

3. A composition for producing pain relief in a body region by introduction of said composition under the skin, and composition consisting essentially of:

a sterile, stable suspension of butyl aminobenzoate in a non-toxic, carrying medium in which said butyl aminobenzoate is substantially insoluble;

said carrying medium consisting essentially of water as the major constituent and a suspending agent composed of (a) polyethylene glycol and (b) a wetting agent for said butyl aminobenzoate;

said butyl aminobenzoate being present in effective amounts up to about 15 wt. % of said suspension;

said polyethylene glycol constituting about 1 to 10 wt. % of said suspension and being present in an amount sufficient to reduce substantially the tendency of said butyl aminobenzoate to settle in said carrying medium;

said wetting agent being present in an amount sufficient to prevent said butyl aminobenzoate from floating in said carrying medium;

the ratio of (a) said polyethylene glycol to (b) said wetting agent being at least about 50/1.

4. A composition as recited in any of claims 1 to 3 wherein:

said polyethylene glycol has a molecular weight in the range 1000 to 5000.

5. A composition as recited in claim 1 or 2 wherein: said polyethylene glycol constitutes about 1 to 10 wt. % of said suspension.

6. A composition as recited in any of claims 1 to 3 wherein:

said wetting agent is polysorbate 80.

7. A composition as recited in claim 6 wherein:

said polyethylene glycol constitutes about 1.0–2.5 wt. % of said suspension;

and said polysorbate 80 constitutes about 0.01–0.05 wt. % of the suspension.

8. A composition as recited in claim 7 wherein:

said polyethylene glycol has a molecular weight in the range 3000 to 3750.

9. A composition as recited in claim 6 wherein:

the ratio of (a) polyethylene glycol to (b) polysorbate 80 is in the range of about 50/1 to about 125/1.

10. A composition as recited in claim 9 wherein:

said ratio of (a) polyethylene glycol to (b) polysorbate 80 is in the range of about 75/1 to about 100/1;

and said polyethylene glycol has a molecular weight in the range 1000 to 5000.

11. A composition as recited in any of claims 1 to 3 wherein said composition is useful for non-toxic injection around a nerve proximal to the body region where relief from pain is desired.

12. A composition for producing pain relief in a body region by introduction of said composition under the skin, and composition consisting essentially of:

a sterile, stable suspension of butyl aminobenzoate in a non-toxic, carrying medium in which said butyl aminobenzoate is substantially insoluble;

said carrying medium consisting essentially of water as the major constituent and a suspending agent comprising polysorbate 80;

said butyl aminobenzoate being present in an effective amount up to about 15 wt. % of said suspension;

said polysorbate 80 constituting about 0.01 to about 0.05 wt. % of said suspension to prevent said butyl aminobenzoate from floating in said carrying medium.

13. A composition as recited in any of claims 1–3 wherein:

said butyl aminobenzoate constitutes about 2.5–5.0 wt. % of said suspension.

14. A composition as recited in claim 13 wherein: said wetting agent is polysorbate 80.

15. A composition as recited in claim 14 wherein: said polysorbate 80 constitutes about 0.005–0.05 wt. % of said suspension.

16. A composition as recited in claim 12 wherein: said butyl aminobenzoate constitutes about 2.5–5.0 wt. % of said suspension.

17. A composition as recited in claim 12 wherein:

said butyl aminobenzoate constitutes about 2.5–5.0 wt. % of said suspension;

said suspending agent comprises about 0.05 to about 0.5 wt. % polyethylene glycol having a molecular weight in the range 1000 to 5000;

and the ratio of polyethylene glycol to polysorbate 80 is at least about 50 to 1.

18. A composition as recited in claim 12 wherein:

said suspending agent further comprises an additional ingredient for reducing substantially the tendency of said butyl aminobenzoate to settle in said carrying medium.

19. A composition for producing pain relief in a body region by introduction of said composition under the skin, said composition consisting essentially of:

a sterile, stable suspension of butyl aminobenzoate in a non-toxic, carrying medium in which butyl aminobenzoate is substantially insoluble;

said carrying medium consisting essentially of water as the major constituent and a suspending agent composed of (a) polyethylene glycol having a molecular weight in the range 1000 to 5000 and (b) polysorbate 80;

said butyl aminobenzoate constituting about 2.5–5.0 wt. % of said suspension;

said polyethylene glycol being present in an amount sufficient to reduce substantially the tendency of said butyl aminobenzoate to settle in said carrying medium;

said polysorbate 80 being present in an amount sufficient to prevent said butyl aminobenzoate from floating in said carrying medium;

the ratio of polyethylene glycol to polysorbate 80 being at least 50 to 1.

20. A composition as recited in claim 19 wherein:
said butyl aminobenzoate constitutes about 2.5 wt. % of said suspension.

21. A composition as recited in claim 19 wherein:
said butyl aminobenzoate constitutes about 5.0 wt. % of said suspension.

22. A composition as recited in any of claims 18–21 wherein:
said polysorbate 80 constitutes about 0.005–0.05 wherein:
and said polyethylene glycol constitutes about 0.5–5.0 wt. % of said suspension.

23. A method for preparing a stable, sterile suspension of butyl aminobenzoate in a non-toxic carrying medium consisting essentially of water as the major constituent and a suspending agent composed of (a) polyethylene glycol and (b) a wetting agent for said butyl aminobenzoate, with the ratio of (a) to (b) being at least about 50/1, said method comprising:

placing at least said butyl aminobenzoate and said polyethylene glycol in a sealed container including mechanical milling structure in the form of (1) a magnetic stirring bar or (2) milling balls;

sterilizing the contents of said sealed container while said contents are in said sealed container;

cooling said sealed container and its contents, after said sterilizing step;

precipitating butyl aminobenzoate particles during said cooling step;

milling said butyl aminobenzoate particles in said sealed container until said particles have a mean size in the range of about 5 to 50 microns;

and adding said wetting agent to the contents of said container (a) before said sterilizing step or (b) after said sterilizing step and before said milling step or (c) after said milling step;

said milling step comprising either magnetically stirring or ball milling the contents of said container, without employing a freeze/fracture procedure.

24. A method as recited in claim 23 wherein;
said wetting agent is polysorbate 80.

25. A method for preparing a stable, sterile suspension of butyl aminobenzoate, in an effective amount up to 15 wt. %, suspended in a non-toxic carrying medium consisting essentially of water as the major constituent and a suspending agent for said butyl aminobenzoate, said method comprising the steps of:

placing said butyl aminobenzoate and said suspending agent in a sealed container including mechanical milling structure in the form of (1) a magnetic stirring bar or (2) milling balls;

sterilizing the contents of said container while said contents are in said sealed container;

cooling said sealed container and its contents, after said sterilizing step;

precipitating butyl aminobenzoate particles during said cooling step;

and milling said butyl aminobenzoate particles in said sealed container until said particles have a mean size in the range of about 5 to 50 microns;

said milling step comprising either magnetically stirring or ball milling the contents of said container, without employing a freeze/fracture procedure.

26. A method as recited in claim 25 wherein:
said suspending agent comprises (a) polyethylene glycol having a molecular weight of at least 1000 and (b) polysorbate 80 in a ratio of (a) to (b) in the range of about 50/1 to about 125/1.

* * * * *

UNITED STATES PATENT AND TRADEMARK OFFICE
CERTIFICATE OF CORRECTION

PATENT NO.    : 5,206,267
DATED         : April 27, 1993
INVENTOR(S)   : Morton Shulman It is certified that error appears in the above-indentified patent and that said Letters Patent is hereby corrected as shown below:

Col. 2, <u>line 40</u>,     after "-" add --50--.

Col. 7, <u>line 48</u>,     after "in" add --an--.

Col. 7, <u>line 49</u>,     change "amounts" to --amount--.

Signed and Sealed this

Twenty-second Day of February, 1994

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,206,267
DATED : April 27, 1993
INVENTOR(S) : Morton Shulman

It is certified that error appears in the above-indentified patent and that said Letters Patent is hereby corrected as shown below:

Col. 2, line 40,  after "-" add --50--.

In the Claims:

Col. 7, line 48,  after "in" add --an--.

Col. 7, line 49,  change "amounts" to --amount--

Col. 9, line 28,  delete "wherein" and add --wt.% of said suspension--.

This Certificate supersedes Certificate of Correction issued February 22, 1994.

Signed and Sealed this

Twelfth Day of April, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,206,267
DATED : April 27, 1993
INVENTOR(S) : Morton Shulman

It is certified that error appears in the above-identified patent and that said Letters Patent is hereby corrected as shown below:

Col. 8, lines 53-54, change "0.05 to about 0.5 wt. % to -- 0.5 to about 5.0 wt. % --.

Signed and Sealed this

Fourth Day of July, 1995

Attest:

BRUCE LEHMAN

Attesting Officer

Commissioner of Patents and Trademarks